United States Patent [19]  
Simon et al.

[11] Patent Number: 4,602,089  
[45] Date of Patent: Jul. 22, 1986

[54] PROCESS FOR PREPARING PURINE COMPOUNDS

[75] Inventors: Lionel N. Simon, Santa Ana, Calif.; Hans-Rudolf Mueller; Hans Zutter, both of Schaffhausen, Switzerland

[73] Assignee: Newport Pharmaceuticals, Inc., Newport Beach, Calif.

[21] Appl. No.: 582,229

[22] Filed: Feb. 21, 1984

Related U.S. Application Data

[62] Division of Ser. No. 357,679, Mar. 12, 1982, Pat. No. 4,451,728.

[51] Int. Cl.⁴ .................... C07D 473/02; A61K 31/52
[52] U.S. Cl. .................... 544/265; 544/276; 544/277; 514/262; 548/337
[58] Field of Search ........ 544/276, 277, 265; 424/251; 514/262

[56] References Cited

U.S. PATENT DOCUMENTS 2,844,576 7/1958 Golman et al. .................... 544/276
3,857,842 12/1974 Asai et al. ........................ 544/276

Primary Examiner—Nicholas S. Rizzo  
Attorney, Agent, or Firm—Cushman, Darby & Cushman

[57] ABSTRACT

There are prepared compounds of the formulae

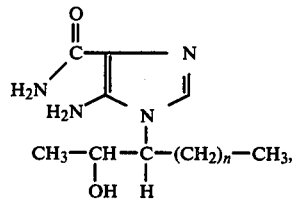

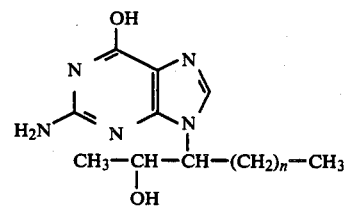

or

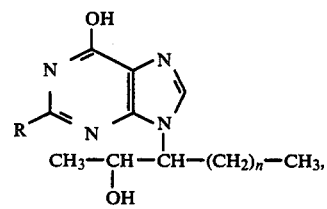

where R is lower alkyl, chlorine, or bromine and n is an integer from 1 to 5. The compounds of formula (1) can be used to make erythro-9-(2-hydroxy-3-nonyl) hypoxanthine and its homologues and also to make the compounds of formulae (2) and (3). All three classes of compounds are useful as immunomodulators.

14 Claims, 2 Drawing Figures

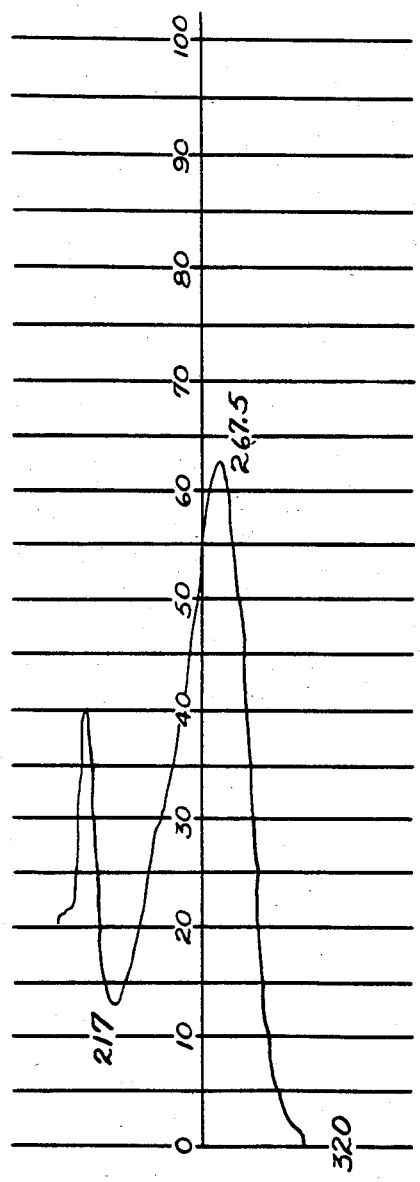

PROCESS FOR PREPARING PURINE COMPOUNDS

This is a division, of application Ser. No. 357,679 filed Mar. 12, 1982 now U.S. Pat. No. 4,451,728.

BACKGROUND OF THE INVENTION

Simon U.S. Pat. Nos. 4,221,909 and 4,221,911 and Giner-Sorolla U.S. Pat. No. 4,221,910 and Faanes International Journal of Immunopharmacology, Vol. 2, No. 3, page 197 (1980), Florentine, International Journal of Immunpharmacology, Vol. 2, No. 3, page 240 (1980), Hadden, International Journal of Immunopharmacology, Vol. 2, No. 3, page 198 (1980), Pahwa, International Journal of Immunopharmacology, Vol. 2, No. 3, page 199 (1980), Wybran, International Journal of Immunopharmacology, Vol. 2, No. 3, page 201 (1980) and Simon, 4th International Congress of Immunology, Paris (1980) show that erythro-9-(2-hydroxy-3-nonyl)-hypoxanthine (NPT 15392), as well as other members of the series described in the patents cited above are potent immunomodulating agents which have been demonstrated to enhance depressed immunity in both animals possessing tumors, Sato, International Journal of Immunopharmacology, Vol. 2, No. 3, page 200 (1980), as well as in humans with various tumors, Simon, American Chemical Society Book of Abstracts, 182nd American Chemical Society Meeting (1981). While the synthesis of these therapeutically useful agents can be carried out by the methods described in the patents cited above, their production, e.g. the production of NPT 15392, on a large scale using those methods was cumbersome, costly, and time consuming. The entire disclosure of the three U.S. patents are hereby incorporated by reference and relied upon.

SUMMARY OF THE INVENTION

There are prepared compounds of the formulae

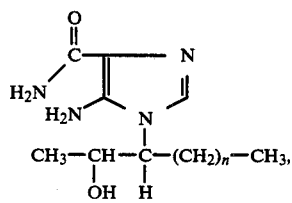
(1.)

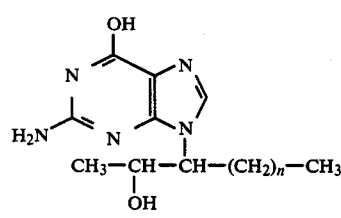
(2.)

or

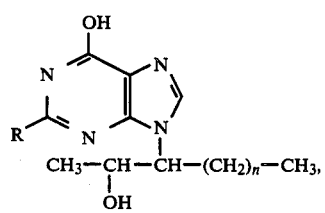
(3.)

where R is lower alkyl, e.g. of 1 to 4 carbon atoms such as methyl, ethyl, propyl, or butyl or halogen of atomic weight 35 to 80, i.e. chlorine or bromine.

The compound erythro-3-(2-hydroxy-3-nonyl)-4-amino-imidazole-5-carboxamide (NPT 15459) is useful in producing NPT 15392 and its homologues of formula (1) above are useful in making the corresponding homologues of NPT 15392. In addition to being useful in making NPT 15392 and its homologues, NPT 15459 and its homologues are useful in preparing novel analogues of NPT 15392 (and its homologues which contain various functional groups in the 2-position of the purine ring, e.g. the compounds of formulae (2) and (3). Such derivatives would be difficult to prepare without the aid of NPT 15459 and its homologues.

The compounds of formula (1), (2), and (3) also have immunomodulating or immunopotentiating activity.

An immunopotentiator or immunomodulator is any agent which either restores depressed immune function, or enhances normal immune function, or both. Immune function is defines as the development and expression of humoral (antibody-mediated) immunity, cellular (thymocyte-mediated) imunity, or macrophage and granulocyte mediated resistance. It logically includes agents acting directly on the cells involved in the expression of immune response, or on cellular or molecular mechanisms which, in turn, act to modify the function of cells involved in immune response. Augmentation of immune function may result from the action of an agent to abrogate suppressive mechanisms derived by negative-feedback influences endogenous or exogenous to the immune system. Thus, immune potentiators have diverse mechanisms of action. Despite the diversity of cell site of action and biochemical mechanism of action of immunopotentiators, their applications are essentially the same; that is, to enhance host resistance.

APPLICATIONS OF IMMUNOPOTENTIATORS (1) The principal protective function of the immune system relates to resistance to invasion by pathogens, including viruses, rickettsia, mycoplasma, bacteria, fungi, and parasites of all types. Thus, improvement of immune response, particularly when depressed, would calculatedly improve resistance in infection or infestation by any of the above pathogens. An immunopotentiator alone or in combination with anti-infective therapy can be applied to any and all infectious diseases.

(2) A second protective function of the immune system is thought to be resistance to engraftment of foreign tissue, either natural as in the fetal-maternal relationship; or unnatural as performed by the transplant physician. Immunopotentiators can also be used to facilitate rejection of fetal or placental tissues or to modify or induce tolerance to grafts.

(3) A third protective function of the immune system is thought to be resistance to malignant cell development as in cancer. The use of immunopotentiators can be used in cancer treatment to enhance tumor rejection and to inhibit tumor recurrences following other forms of therapy.

(4) A fourth protective function involves the capacity to recognize foreignness and to maintain nonreactivity to self by positive suppressor mechanisms. In autoimmune and related disorders, immune reactivity directed at self antigens or exagerrated, elevated responses are apparent which are self-destructive. Immunopotentiators can be used to restore normal suppressor mechanisms, induce tolerance, or otherwise promote a normal immune response.

Each of the protective functions of the immune system can be modified by non-specific therapy with immunopotentiators alone or in combination with other agents employed to improve resistance or to kill the invading pathogen. In addition, specific resistance can be augmented by use of immunopotentiators in conjunction with some form of antigen as in a vaccine employing, for example, virus, tumor cells, etc. This use can be to induce either specific immunity or tolerance. The latter might be exemplified by use with antigen in allergy or auto-immune diseases. Use of immunopotentiators may be either therapeutic or prophylactic; the latter particularly in aging, where infection, auto-immunity, and cancer are more common. The timing of administration and routes are variable and may be critical in determining whether a positive or negative response results. Any agent capable of augmenting immune response may inhibit it depending on timing and dose; thus, under certain circumstances an immunopotentiator could be used as an immunosuppressive agent for use in allergy, auto-immunity and transplantation.

Various procedures for determining immunomodulationg activity are shown in Simon E.P.O. published application No. 0036077, the entire disclosure of which is incorporated by reference and relied upon.

Illustrative of compounds within the invention in addition to NPT 15459 are:

erythro-3-(2-hydroxy-3-amyl)-4-aminoimidazole-5-carboxamide,
erythro-3-(2-hydroxy-3-hexyl)-4-aminoimidazole-5-carboxamide,
erythro-3-(2-hydroxy-3-heptyl)-4-aminoimidazole-5-carbozamide,
erythro-3-(2-hydroxy-3-octyl)-4-aminoimidazole-5-carboxamide,
erythro-9-(2-hydroxy-3-nonyl)-2-aminohypoxanthine,
erythro-9-(2-hydroxy-3-amyl)-2-aminohypoxanthine,
erythro-9-(2-hydroxy-3-hexyl)-2-aminohypoxanthine,
erythro-9-(2-hydroxy-3-heptyl)-2-aminohypoxanthine,
erythro-9-(2-hydroxy-3-octyl)-2-aminohypoxanthine,
erythro-9-(2-hydroxy-3-nonyl)-2-chlorohypoxanthine,
erythro-9-(2-hydroxy-3-amyl)-2-chlorohypoxanthine,
erythro-9-(2-hydroxy-3-hexyl)-2-chlorohypoxanthine,
erythro-9-(2-hydroxy-3-heptyl)-2-chlorohypoxanthine,
erythro-9-(2-hydroxy-3-octyl)-2-chlorohypoxanthine,
erythro-9-(2-hydroxy-3-nonyl)-2-bromohypoxanthine,
erythro-9-(2-hydroxy-3-amyl)-2-bromohypoxanthine,
erythro-9-(2-hydroxy-3-nonyl)-2-methylhypoxanthine,
erythro-9-(2-hydroxy-3-amyl)-2-methylhypoxanthine,
erythro-9-(2-hydroxy-3-hexyl)-2-methylhypoxanthine,
erythro-9-(2-hydroxy-3-heptyl)-2-methylhypoxanthine.
erythro-9-(2-hydroxy-3-octyl)-2-methylhypoxanthine,
erythro-9-(2-hydroxy-3-nonyl)-2-ethylhypoxanthine.
erythro-9-(2-hydroxy-3-hexyl)-2-ethylhypoxanthine, and
erythro-9-(2-hydroxy-3-amyl)-2-ethylhypoxanthine.

BRIEF DESCRIPTION OF THE DRAWINGS

FIG. 2 is the UV-spectrum of NPT 15459.

DETAILED DESCRIPTION

Figure 1:
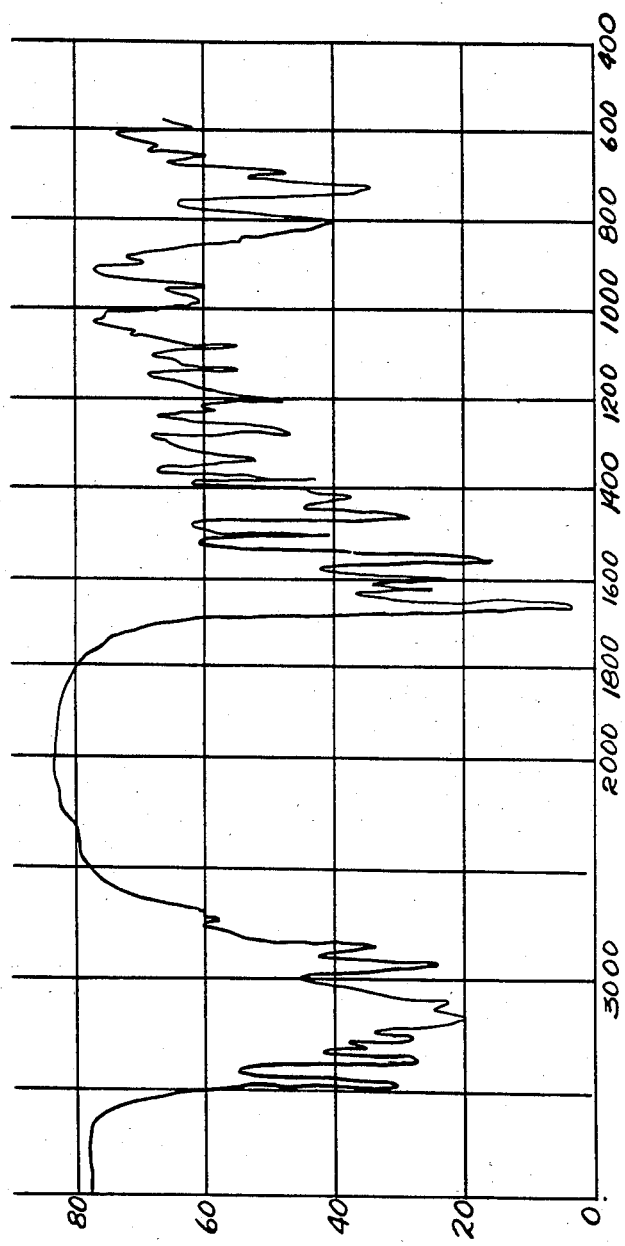
FIG. 1 is the IR-spectrum of NPT 15459.

The synthesis of NPT 15459 is carried out according to the scheme presented below:

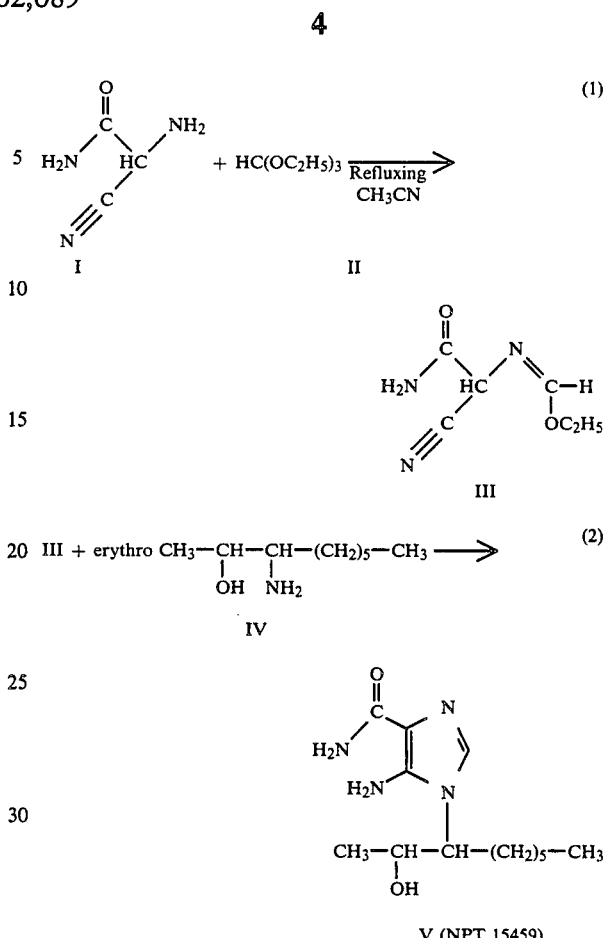

The other compounds within formula (1) can be prepared in the same manner by replacing erythro-3-amino-2-nonanol by the corresponding aminoalcohol, e.g. erythro-3-amino-2-pentanol and erythro-3-amino-2-octanol. In place of ethyl orthoformate there can be used other lower alkyl orthoformates, e.g. methyl orthoformate, propyl orthoformate and butyl orthoformate.

EXAMPLE 1

Synthesis of Erythro-3-(2-hydroxy-3-nonyl)-4-amino-imidazole-5-carboxamide (NPT 95459 (V))

For improved yield, reactions (1) and (2) above are carried out sequentially without isolation of the intermediate product III. 2-amino-2-cyanoacetamide (1) (171 g, 1.71 moles) is suspended in 2200 ml of acetonitrile. Orthoformic acid triethylester (II) (334 ml-2.0 moles) and 2 ml of pyridine are added to the suspension with stirring. The suspension is heated to reflux temperature, using an oil bath preheated to 100° C. The suspension is held at boiling temperature for 40 to 60 minutes. III is produced in situ. 272.5 g of erythro-3-amino-2-nonanol (IV) (1.71 moles) are then added over a 3 to 5 minute period and boiling is continued for an additional 10 to 15 minutes. The reaction is quickly chilled to room temperature. The erythro-3-(2-hydroxy-3-nonyl)-4-amino-imidazole-5-carboxamide (NPT 15459) (V) crystallizes. It is filtered by suction, washed with a small amount of acetonitrile and dried in vacuo at 70° C.

Yield: 330.4 g, 72% of theory

Melting point (after recrystallization from acetonitrile): 154°–158° C.

SUMMARY OF CHEMICAL PROPERTIES OF (NPT 15459)

| Chemical or Physical Property | Value | |
|---|---|---|
| M.P. | 154-158° C. | |
| C | Theory: 58.18 | Found: 57.80 |
| N | Theory: 20.87 | Found: 21.00 |
| Solubility | soluble-isopropanol | |
| | very soluble - HCl (Aq), acetic acid, methanol, ethanol | |
| | insoluble - benzene, water | |
| TLC | silica gel (ethylacetate/methanol; 8:2) Rf = 0.61 | |
| Mol. Wt. | 268.35 | |
| Appearance | Colorless and odorless powder | |

Identity

1. IR-spectrum: (FIG. 1)

| | | |
|---|---|---|
| bands at 3450 cm$^{-1}$ | | (—NH$_2$) |
| 3400–3100 cm$^{-1}$ | (several) | (—CONH$_2$ a.o.) |
| 2950 cm$^{-1}$ | | (—CH$_3$—, —CH$_2$—) |
| 1660 cm$^{-1}$ | | (—imidazole) |

2. UV-spectrum: (FIG. 2)

maximum at 267 nm
minimum at 217 nm

| | | Nominal Value: |
|---|---|---|
| Sulphate Ash | Found | <0,5% |
| | not ponderable | |
| Heavy Metals | <50 ppm | ≦50 ppm |
| Loss of Drying | Found | ≦2% |
| | not ponderable | |
| Purity (TLC) | no side spots | no side spots |
| Percentage of Side Products | <0, 2 mole % | ≦10 mole % |
| Content | 98, 7% | 95–105% |

Utilization of NPT 15459 to Produce NPT 15392

The reaction scheme described below illustrates the use of NPT 15459 in the synthesis of NPT 15392;

Reaction Scheme:

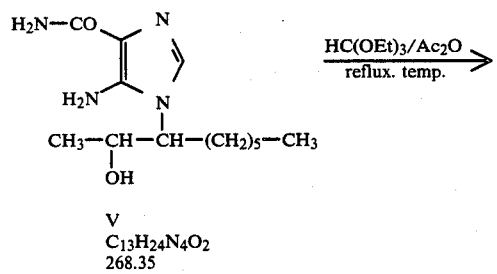

V
C$_{13}$H$_{24}$N$_4$O$_2$
268.35

-continued
Reaction Scheme:

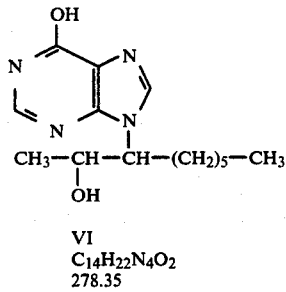

VI
C$_{14}$H$_{22}$N$_4$O$_2$
278.35

The homologues of NPT 15392 can be prepared in the same manner from the corresponding homologues of NPT 15459. In place of ethyl orthoformate there can be employed the other lower alkyl orthoformates, e.g. the methyl, propyl, and butyl orthoformates. In forming NPT 15392 the acetic anhydride forms the acetate of NPT 15392 and this is then hydrolized with alkali, e.g. sodium hydroxide.

In place of an orthoformic acid ester formic acid can also be used.

EXAMPLE 2

Utilization of NPT 15459 to Produce NPT 15392 (Erythro-9-(2-hydroxy-3-nonyl)hypoxanthine)

415 g of erythro-3-(2-hydroxy-3-nonyl)-4-aminoimidazole-5-carboxamide (V) (1.55 moles) are suspended in 385 ml of orthoformic acid triethylester. 220 ml of acetic acid anhydride are added with stirring. The suspension that is obtained is heated with stirring up to 100°–105° C. An exothermic reaction ensues with liberation of ethanol. The liberated ethanol is separated by distillation. The temperature of the reaction mixture is increased slowly up to 130°–140° C. Stirring is continued for about 3 hours, while the liberated ethanol is continuously separated by distillation. The reaction mixture is concentrated to a viscous syrup, which is stirred into a mixture of 415 of 30% aqueous NaOH and 1.68 liter of water. The brown solution is slightly acidified by addition of a solution of 123 ml of acetic acid in 1.5 liter of water. Erythro-9-(2-hydroxy-3-nonyl)-hypoxanthine (VI) crystallizes, is filtered by suction, washed with water and dried in vacuo at 60° C.

Yield: 350 g corresponding to 81.4% of theory

Melting point (after repeated recrystallization from aqueous ethanol): 200°–201° C.

Content by titration: 99.4%

Content of threo isomer: 0.9%

Utilization of NPT 15459 to Produce Novel Derivatives of NPT 15392

NPT 15459 and its homologues possess the ability to react with a variety of reagents which could lead to ring closure and the production of novel purine derivatives. By the judicious choice of reagents, it is possible to produce a number of 2-substituted derivatives of NPT 15392 and its homologues that could not be produced by other means. The scheme provided in the following diagram illustrates a number of such examples.

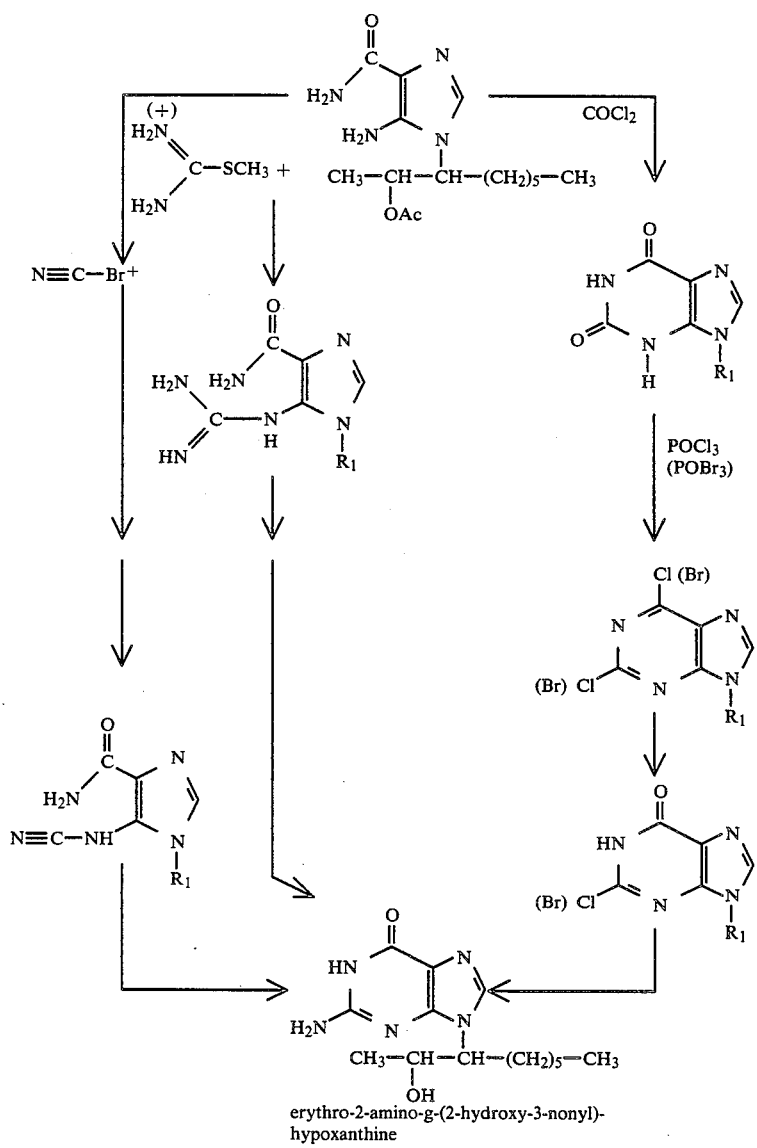

erythro-2-amino-g-(2-hydroxy-3-nonyl)-hypoxanthine

In the reaction scheme just set forth $R_1$ is the group

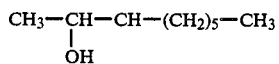

The 2,6-dichloro-purine compound in the above scheme can be converted to the 2-chloro hypoxanthine using conventional procedures, e.g. by refluxing with sodium hydroxide in the manner shown in Simon U.S. Pat. No. 4,221,909 Method D. The latter compound can then be converted to the corresponding 2-amino-hypoxanthine by reacting with methanolic ammonia in a manner analogous to that shown in Simon U.S. Pat. No. 4,221,909 Method B.

Compounds of formula (3) where R is methyl can be made by reacting NPT 15459 or its homologues with ethyl orthoacetate rather than ethyl orthoformate. Compounds of formula (3) where R is ethyl can be made in similar manner by reacting NPT 15459 with ethyl orthopropionate.

The immunomodulating activity of NPT 15459 was determined. The results are set forth below in Tables 1 and 2.

In Table 1 the effect of NPT 15459 on Con A Induced Proliferation is described. The procedure is described in Simon U.S. Pat. No. 4,221,909, column 24, line 12 to column 25, line 10.

In Table 1 the effect of NPT 15459 on LPS Induced Proliferation is described and the procedure is described as follows.

PROCEDURE

Murine Splenocyte Stimulation with Concanavalin A (Con A), Lipopoylsaccharide (LPS), and Allogeneic Splenocytes (MLC).

A. Solutions Preparation
  1. Supplemented RPMI-1640
    a. RPMI-1640 (GIBCO)—500 ml bottle(s) stored at 4° C.
    b. HEPES buffer (Flow)—powder stored at 4° C.
    c. AM (Antibiotic-Antimycotic, GIBCO), penicillin 10,000 U/ml, fungizone 25 mcg/ml, streptomycin 10,000 mcg/ml aliquoted in 5 ml and stored at −20° C.
   d. L-glutamine (GIBCO, 200 mM), aliquoted in 5 ml and stored at −20° C.

Add 5 ml AM and 5 ml L-glutamine to each 500 ml bottle of RPMI-1640. Add ∼10 ml RPMI to 1.79 g HEPES and vortex until completely dissolved. Filter HEPES solution with 10 ml syringe through 0.22 μm Acrodisc filter and add to 500 ml bottle of RPMI-1640. Allow to warm to room temperature before use.

2. Fetal Calf Serum (FCS, Microbiological Associates) aliquoted in 2 ml and stored at −70° C.
3. Mitomycin C (Calbiochem)—50 mg/667 ml supplemented RPMI-1640, aliquoted, and stored at −70° C. Keep tube wrapped in foil until used in assay.
4. PBS (Oxoid Ltd.)—5 tablet/500 ml distilled water, autoclave and store at 4° C.
5. Con A (Calbiochem)—100 mg/ml NaCl injection solution (McGaw), filter, aliquot in 1 ml, and store at 31 70° C.
6. LPS (Sigma, *E. coli* serotype #011:B4)—∼1 mg/ml. Supplement RPMI-1640 with AM and L-glutamine. Remove∼10 ml for dissolving HEPES (0.358 G) and filter HEPES solution. Add four 25 mg bottles of LPS to remaining media and incubate at 37° C. for 1 hour. Filter through 0.22 μm filters, add filtered HEPES, aliquot in 2 ml and store at −70° C.
7. NPT-15392—Add 500 mg/500 ml NaCl injection solution (McGaw), and incubate in 45° C. waterbath for 1 hour. Filter through 0.22 μm filter followed by 0.025 μm filter. Autoclave at 15 psi (250° C.) for 15 minutes. Dilute an aliquot 1:25 in 0.1 N HCl and read absorbance at 250 λ on spectrophotometer. Calculate concentration from the following equation:

$$(O.D./11.42) \times 25 \text{ (or appropriate dilution)} \times 278 = \mu g/mL$$

Aliquot in various volumes and store at −20° C.
8. Tritiated thymidine ($^3$H-TdR, Schwartz-Mann, 6 Ci/mM). Remove a slightly larger volume of $^3$H-TdR than needed from vial with a 1 cc syringe and place volume in the cap of a small sterile plastic tube. Pipet volume necessary for a 1:100 dilution into a tube with appropriate volume of warmed supplemented RPMI-1640 saved from cell assay. Vortex thoroughly before adding to plates. Dispose of all radioactive materials in radioactive container.
9. Toluscint—77 ml Scintiprep/1 gal toluene B. Equipment
1. 100 mesh stainless steel screens. Cut out ∼3" squares and press into centrifuge tube carriers with bottom of 50 ml plastic tube using twisting motion. Autoclave.
2. Sterile Plastic Tubes
   12×75 mm, 5 ml Falcon tubes
   17×100 mm, 15 ml Falcon tubes
   15 ml graduated conical centrifuge tubes
   16×125 mm screw-cap tubes
   50 ml graduated conical centrifuge tubes
3. Pasteur pipets and bulbs.
4. Plastic serological pipets—1, 5, and 10 ml.
5. Pipet aid.
6. Micropipetters and pipette tips (autoclaved).
7. Two-inch square guaze pads (autoclaved).
8. Plastic syringes—1, 3, and 10 cc.
9. Gelman Acrodisc filters—0.2 μm.
10. Falcon 50 filters—0.22 μm.
11. Millipore 0.2 and 0.025 μm filters and filter assembly.
12. Titertek, multi-channel pipetter.
13. 25 g 5/8 hypodermic needles.
14. 70% ethanol.
15. 0.9% saline (filtered).
16. Distilled water (filtered).
17. Scintiprep.
18. Toluene.
19. Kimble 15×45 mm, 1 dram vials.
20. Sterile cryogenic tubes.
21. Centrifuge.
22. $CO_2$ incubator.
23. Biological safety hoods.
24. Liquid scintillation counter.
25. Coulter counter.
26. Isoton (Diluid-Azide free, J. T. Baker).
27. CyMet—Automated (J. T. Baker).
28. Isoterge II—Azide free (CMS).
29. Coulter Counter Reference Standards (CH . 60 Hematology Control Dual Pak, Dade).
30. Coulter counter vials (VWR).
31. Heavy-duty lab stirrer with teflon-tipped pestle.

C. Animal Injections
1. Thaw drug to room temperature. Filter through 0.22 μm filter. Dilute in NaCl injection solution to appropriate concentration(s). Aliquot and store at 4° C. until use. On day of use, warm drug to room temperature. Swab animal at area of injection with 70% ethanol and sterile guaze. Inject 0.5 ml i.p. alternating sides each day.

D. Animal Sacrifice and Cell Preparation
1. Animals are sacrificed by cervical dislocation killing one from each group and processing the cells individually before killing the next animal. Swab each animal with 70% ethanol before surgery. Carefully remove the spleen, trimming away any lipid tissue, and place in a 16×125 mm screw-cap tube with a few ml of supplemented RPMI-1640. Use 8 vertical strokes (or enough to break up all tissue) with teflon-tipped homogenizer. Filter each sample through a 100 mesh screen into a 50 ml tube. Transfer cells into a 15 ml (11×100 mm) tube and fill to top with supplemented RPMI-1640. Centrifuge for 2 minutes at 1700 RPM and resuspend with 5 ml supplemented RPMI-1640. After all samples have been spun, vortex each briefly and let sit for 1 hour. Vortex each sample ∼5 seconds, waiting ∼10 seconds between each sample. Let sit 5 minutes, then pipet cell suspension into 5 ml (12×75 mm) tube being careful not to remove any sediment. Remove 50 μl cell suspension using micropipetter, carefully wipe pipet tip with Kimwipe and pipet into 20 ml Isoton in Coulter counter vial, rinsing pipet several times in the Isoton. Add 6 drops of CyMet and swirl vial to mix. Use the following Coulter counter settings: Amplification-1, Threshold-10, and Aperture Current-1. Clean counter with Isoterge the morning of experiment and count background before standardizing with CH . 60 Hematology Controls. After cell counts are obtained, dilute to $6 \times 10^6$ cells/ml with supplemented RPMI and aliquot into 3 tubes for the 3 assays.

E. Mitogen Assays
1. Pipet 100 μl control media (supplemented RPMI) or appropriate dilution of mitogen (starting with lowest concentration) into microtiter plate using Titertek. Place plates in 37° C. $CO_2$ incubator with $CO_2$ set at 0.5 after each plate has been pipetted. Pipet 100 μl responder cells into wells starting with most dilute mitogen concentration. Place plates in incubator as they are filled and after all plates are in incubator, let sit for 10–20 minutes. Wrap plates with plastic wrap, recover with top, replace in incubator, and reset $CO_2$ to ~0.05. Save ~50 ml supplemented RPMI at 4° C. for thymidine dilution. After ~44 hours warm the RPMI to 37° C. in incubator. Dilute tritiated Thymidine 1:100 in warmed RPMI. Use Titertek to add 50 μl Thymidine to each well. Treat plates as above and incubate overnight (~18 hours).

F. Cell Harvest
1. Rinse lines of cell harvester well before harvesting plates. Using a new filter strip for each row, wash each row 20 times with saline and 20 times with water. Place strips on labeled styrofoam board and dry under infrared lamp for ~1 hour. Cut out sample discs on disc-cutter into scintillation vials, add ~2 ml toluscint with automatic dispenser, and cap vials while still in the metal tray. Put vials in scintillation counter and count using Program #3.

G. MLC Cell Preparation
1. Use responding cells prepared for Con A and LPS assays and prepare allogeneic cells with C57BL/6 mice. Kill animals and homogenize cells as in step D. Transfer cells into 15 ml Falcon tube (11×100) and fill to top with RPMI-1640 medium. Centrifuge for 1½ minutes at 1,700 RPM. Do another wash at 1,700 RPM for 1½ and resuspend in 2 ml of RPMI-1640. Pool the cells from all allogeneic mice. Let the clumps settle on the bottom of the tube for five minutes. Carefully remove the supernate from the clumps of cells.
2. Perform a cell count as in step D and dilute cells to give $180 \times 10^6$ cells/6 ml of RPMI medium.
3. While vortexing, add 0.2 ml of MitC to the cells. Incubate at 37° C. with 5% $CO_2$ for 30 minutes. During incubation, mix the cells gently every 10 minutes.
4. At the end of 30 minutes incubation, dilute the cells with RPMI-1640 medium to top of 15 ml Falcon tube. Centrifuge at 1,700 RPM for 1½ minutes. Pour supernate off and remove the last few drops by touching the edge of the tube on a piece of sterile gauze.
5. First Wash: Add 3–5 ml of RPMI medium and vortex at setting #3 for 10–20 seconds. Fill the tube with RPMI-1640 medium and centrifuge at 1,700 RPM for 1½ minutes.
6. Second Wash: Pour supernate off and touch edge of tube on sterile gauge to remove last few drops. Add 3–5 ml of RPMI and vortex at #3 setting for 10–20 seconds. Fill the tube with RPMI-1640 to the top and let sit for 15 minutes, then centrifuge at 2,000 RPM for 2 minutes.
7. Third Wash: Repeat the second wash. Resuspend in 5 ml of RPMI-1640.
8. Dilute Allogeneic cells to $6 \times 10^6$ cells/ml or $48 \times 10^6$ C/8 ml.
9. Use responding cells of $6 \times 10^6$ cells/ml prepared for Con A and LPS assay.
10. Cell Plating: For each individual animal, plate 2 rows of 3 or 4 wells on 96 well costar plate. First row for Control, use 100 λ of responding cells and 100 λ of RPMI-1640 (supplemented). The second row use 100 λ of responding cells and 100 λ of allogeneic cells.
11. Procedures for incubation, labeling with tritated thymidine, and harvesting the cells are the same as for Con A and LPS assays except for the incubation before labeling time with $^3H$ Thymidine which is 68 hours after cell plating instead of 44 hours. Cell harvesting is done at the usual 18 hours after labeling with $^3H$-Thymidine.

In Table 2 the SRBC Induced Antibody Formation procedure employed was that shown in Simon EPO application No. 0036077 page 46.

TABLE 1

IMMUNOMODULATING ACTIVITY NPT 15459
Mitogen Induced Lymphocyte Proliferation

| Concentration (Dosage) | Test | $\overline{X}$ cpm | Percent Change from Control |
|---|---|---|---|
| Control | Con A Induced Proliferation | 35,059 | 0 |
| .020 μg/ml | Con A Induced Proliferation | 35,747 | +2 |
| .500 μg/ml | Con A Induced Proliferation | 30,920 | −12 |
| 5.0 μg/ml | Con A Induced Proliferation | 20,098 | −43[a] |
| 10.0 μg/ml | Con A Induced Proliferation | 12,736 | −66[a] |
| Control | LPS Induced Proliferation | 7044 | 0 |
| .02 μg/ml | LPS Induced Proliferation | 6184 | −12 |
| .5 μg/ml | LPS Induced Proliferation | 6676 | −6 |
| 5.0 μg/ml | LPS Induced Proliferation | 4128 | −42[a] |
| 10.0 μg/ml | LPS Induced Proliferation | 2449 | −66[a] |

TABLE 2

IMMUNOMODULATING ACTIVITY NPT 15459
Antibody Formation

| Concentration (Dosage) | Test | $\overline{X}$ PFC/$10^6$ Cells | Percent Change from Control |
|---|---|---|---|
| Saline | SRBC Induced Antibody Formation | 53 | 0 |
| .05 mg/kg | | 157 | +196 |
| .5 mg/kg | | 120 | +126 |
| 5.0 mg/kg | | 66 | +24 |

FORMULATIONS

The compounds of the present invention can be fed to a mammal at a dosage of 1–1000 mg/kg of body weight and could be anticipated to be active at levels as low as 0.0005 mg/kg.

It is to be anticipated they may be administered in tablet or capsule form to humans and where solubility permits in the form of an aqueous syrup, or as solutions in oil, or where insoluble as a supension. Typical pharmaceutical formulations are described below:

Capsule:
NPT 15459: 0.1–500 mg

Avicel pH 101 (microcrystalline cellulose): to make 800 mg.

SUSPENSION

Aqueous suspensions can be made with a number of suspending agents incorporated with the active drug substances. Included as suspending agents are such substances as sodium carboxymethylcellulose, Na alginate gum, tragacanth, Avicel RC-591 (microcellulose), methylcellulose, Veegum, Xanthan gum. In addition to a suspending agent such substances as sweetners, flavors, colorants, preservatives, protective colloids, and dispersants may be added.

SYRUP FORMULATION

NPT 15459: 0.05-250 mg (or at maximum level of solubility)
Corn Sugar: 3.25 g.
Distilled Water: 0.05 g.
FD and C Red 40: 0.00175 g.
Sodium Saccharin: 0.00250 g.
Alcohol U.S.P.: 0.08 g.
Methyl paraben U.S.P.: 0.005 g.
Glycerin: 0.001 g.
Cherry flavor: 0.31225 g.
Fruit flavor: 0.00825 g.
Distilled water g.s.ad: 5 ml.

TABLET FORMULATION

NPT 15459: 0.1-500 mg
Avicel pH 101: 130 mg
Starch, modified: 20 mg
Magnesium stearate U.S.P.: 5.5 mg
Polyvinylpyrrolidone: 22 mg
Stearic acid U.S.P.: 30 mg

What is claimed is:

1. A process of preparing a compound of the formula

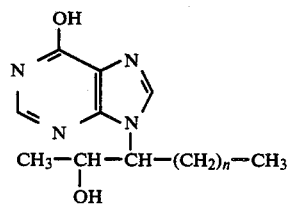

comprising reacting a compound of formula (1)

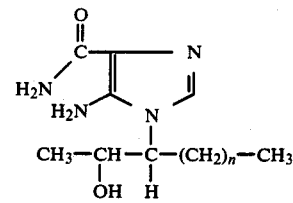

with an equimolar amount of a lower alkyl orthoformate formic acid in the presence of acetic anhydride.

2. A process according to claim 1 wherein n is 5.
3. A process according to claim 2 comprising removing the alcohol formed in the reaction.
4. A process according to claim 3 comprising adding alkali after removing the alcohol to neutralize the acetic anhydride.
5. A process according to claim 4 wherein there is used ethyl orthoformate.
6. A process according to claim 3 wherein there is used ethyl orthoformate.
7. A process according to claim 2 wherein there is used ethyl orthoformate.
8. A process according to claim 1 wherein there is employed a lower alkyl orthoformate.
9. A process according to claim 1 wherein there is employed formic acid.
10. A process of preparing a compound of the formula

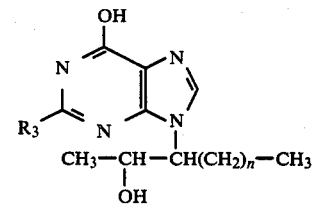

where $R_3$ is hydrogen or lower alkyl comprising reacting a compound of formula (1) of claim 1 with either an equimolar amount of a lower alkyl orthoester of a lower fatty acid or with formic acid in the presence of acetic anhydride.

11. A process according to claim 10 wherein $R_3$ is methyl and there is employed a lower alkyl orthoacetate.
12. A process according to claim 11 wherein there is employed ethyl orthoacetate.
13. A process according to claim 10 wherein $R_3$ is ethyl and there is employed a lower alkyl orthopropionate.
14. A process according to claim 13 wherein there is employed ethyl orthopropionate.

* * * * *